United States Patent
Na et al.

(10) Patent No.: US 9,765,335 B2
(45) Date of Patent: Sep. 19, 2017

(54) GENE NANOCOMPOSITE, AND CELLULAR INTERNALIZATION METHOD OF GENE USING SAME

(71) Applicant: Catholic University of Korea Industry-Academy Cooperation Foundation, Gyeonggi-do (KR)

(72) Inventors: Kun Na, Bucheon-si (KR); Sin Jung Park, Seoul (KR)

(73) Assignee: CATHOLIC UNIVERSITY OF KOREA INDUSTRY-ACADEMIC COOPERATION FOUNDATION, Gyeonggi-do (KR)

( * ) Notice: Subject to any disclaimer, the term of this patent is extended or adjusted under 35 U.S.C. 154(b) by 0 days.

(21) Appl. No.: 14/364,611

(22) PCT Filed: Dec. 11, 2012

(86) PCT No.: PCT/KR2012/010744
§ 371 (c)(1),
(2) Date: Dec. 2, 2014

(87) PCT Pub. No.: WO2013/089411
PCT Pub. Date: Jun. 20, 2013

(65) Prior Publication Data
US 2015/0225723 A1 Aug. 13, 2015

(30) Foreign Application Priority Data
Dec. 12, 2011 (KR) .......................... 10-2011-0133244

(51) Int. Cl.
| | | |
|---|---|---|
| C12N 15/113 | (2010.01) | |
| C12N 13/00 | (2006.01) | |
| A61K 41/00 | (2006.01) | |
| A61K 47/48 | (2006.01) | |
| C12N 15/87 | (2006.01) | |
| A61K 47/59 | (2017.01) | |
| A61K 47/64 | (2017.01) | |
| A61K 47/69 | (2017.01) | |
| A61K 48/00 | (2006.01) | |

(52) U.S. Cl.
CPC ...... *C12N 15/1136* (2013.01); *A61K 41/0057* (2013.01); *A61K 41/0071* (2013.01); *A61K 47/48192* (2013.01); *A61K 47/48207* (2013.01); *A61K 47/48315* (2013.01); *A61K 47/48907* (2013.01); *A61K 47/48923* (2013.01); *A61K 47/59* (2017.08); *A61K 47/595* (2017.08); *A61K 47/645* (2017.08); *A61K 47/6935* (2017.08); *A61K 47/6939* (2017.08); *C12N 13/00* (2013.01); *C12N 15/87* (2013.01); *A61K 48/00* (2013.01); *A61K 48/0041* (2013.01); *C12N 15/113* (2013.01); *C12N 2310/14* (2013.01); *C12N 2320/32* (2013.01); *Y10T 428/2982* (2015.01)

(58) Field of Classification Search
None
See application file for complete search history.

(56) References Cited

FOREIGN PATENT DOCUMENTS

| | | |
|---|---|---|
| KR | 20090091079 A | 8/2009 |
| KR | 20100120473 A | 11/2010 |

OTHER PUBLICATIONS

Choi, et al. (2005) "Synthesis and Functional Evaluation of DNA-Assembled Polyamidoamine Dendrimer Clusters for Cancer Cell-Specific Targeting", Chemistry & Biology, 12(1): 35-43.*
Norum, et al. (2009) "Photochemical internalization of bleomycin is superior to photodynamic therapy due to the therapeutic effect in the tumor periphery", Photochemistry and Photobiology, 85(3): 740-49.*
Hogset, et al. (2002) "Light-induced adenovirus gene transfer, an efficient and specific gene delivery technology for cancer gene therapy", Cancer Gene Therapy, 9(4): 365-71.*
Fouassier, et al. (2002) "Photopolymerization reactions under visible lights: principle, mechanisms and examples of applications", Progress in Organic Coatings, 47: 16-36.*
International Search Report and Written Opinion dated Mar. 27, 2013 for corresponding International Patent Application No. PCT/KR2012/010744, filed Dec. 11, 2012.
International Preliminary Report on Patentability and English Translation of the Written Opinion dated Jun. 17, 2014 for corresponding International Patent Application No. PCT/KR2012/010744, filed Dec. 11, 2012.
Kim, Won Jong: "Gene Delivery System by Polymeric Nanocomplexes", Polymer Science and Technology, 2008, vol. 19, No. 2, pp. 125-129.

* cited by examiner

*Primary Examiner* — Robert M Kelly
(74) *Attorney, Agent, or Firm* — Westman, Champlin & Koehler, P.A.; Z. Peter Sawicki; Amanda M. Prose

(57) ABSTRACT

A gene nanocomposite and a cellular internalization method of a gene using the same are provided. More specifically provided is a gene nanocomposite including: a photosensitizer-conjugated polymer; and one or more materials selected from a gene and a gene/cationic polymer composite, and a cellular internalization method of a gene using the same to improve gene delivery efficiency into a mammal-derived cell and gene expression.

12 Claims, 4 Drawing Sheets

GENE NANOCOMPOSITE, AND CELLULAR INTERNALIZATION METHOD OF GENE USING SAME

CROSS-REFERENCE TO RELATED APPLICATIONS

This application is a Section 371 National Stage Application of International Application No. PCT/KR2012/010744, filed Dec. 11, 2012, the content of which is incorporated herein by reference in its entirety, and published as WO 2013/089411 on Jun. 20, 2013, not in English.

TECHNICAL FIELD

The present invention relates to a gene nanocomposite and a cellular internalization method of a gene using the same, and more particularly, to a gene nanocomposite including a photosensitizer-conjugated polymer and a cellular internalization method of a gene using the gene nanocomposite.

BACKGROUND ART

Gene therapies are approaches for making genes exhibit intrinsic functions by externally inducing normal genes in place of disease-causing genes, and are taken into consideration as methods for curing hereditary diseases and other diseases, such as cardiovascular diseases, immune diseases, endocrine diseases, or cancers. However, in order to achieve effective gene therapies, it is necessary to transfer genes into cells. To this end, research into methods for transmitting genes into cells is being conducted, including a method using a transmitter such as a viral or non-viral vector, a physical method, such as a micro glass capillary injection method, an ultrasonic method or an electroporation method.

In the method of using a transmitter such as a viral or non-viral vector, representative examples of the viral vector include retrovirus, adenovirus, lentivirus, and so on, which are known to be highly infective to have high gene delivery efficiency. However, when the viral vector is inserted into a host chromosome, it is limited in its usage because it causes mutation, creation of infective virus, a possibility of causing an inflammation in the host. Therefore, owing to simplicity or a relatively low risk, numerous studies of the method of using a non-viral vector, such as a cationic polymer, are being made. This method is reportedly advantageous in that genes can be stabilized by forming a complex through electrostatic interaction with negatively-charged genes and intracellular delivery of genes is facilitated by positive charges.

However, when the cationic polymer is used in an amount enough to obtain a sufficient effect, which still is, however, less sufficient than the viral transmitter, it may cause acute toxicity and may make it difficult to achieve transfer specific to a target cell. In addition, since the cationic polymer combines with various proteins in blood, its stability is severely deteriorated, so that it is different to be used in vivo.

Therefore, in order to compensate for the aforementioned shortcomings, a method for solving problems of toxicity and instability in blood has been researched by forming a tertiary complex of a gene/cationic polymer composite and an anionic polymer. However, the tertiary complex of a gene/cationic polymer composite and an anionic polymer considerably reduces gene delivery efficiency while being capable of lowering toxicity. In addition, the tertiary complex still has a technological difficulty in view of target cell specific transfer.

In addition, it has been reported that the non-viral gene transmitter vector and the gene composite are taken up via endocytosis. However, the gene/non-viral vector composite delivered to the endosome by the endocytosis may stay in the endosome to then be fused with lysosome, causing decomposition of the gene by various digestive enzymes present in the lysosome, thereby noticeably lowering the gene delivery efficiency. Therefore, the gene/non-viral vector composite delivered by the endocytosis may be separated from the endosome, so that the capability of the gene/non-viral vector composite moving to the cytoplasm serves as quite an important factor in increasing the gene delivery efficiency.

Meanwhile, photodynamic therapy (PDT) is a technology of treating lesions using a photosensitizer and an appropriate amount of light (photon) even without performing a surgical operation. A porphyrin-series compound, which is typically used as the photosensitizer, is extracted from silkworm powder, mulberry leaves, green algae or the like, has suitable spectroscopic characteristics and may cause electronic transition by green light (700-900 nm) having relatively large cell penetrating capability. When excited by light having a particular wavelength, the photosensitizer may create activated oxygen (e.g., singlet oxygen, oxygen radical, superoxide, peroxide, or the like). The created activated oxygen is involved in oxidation of lipid, protein and hexane and disruption of intracellular structures, resulting in apoptosis.

In addition, a porphyrin derivative as a photosensitizer material is deposited to be selectively to cancer cells. The deposition of the porphyrin derivative is presumably accounted for by receptors for low density lipoprotein (LDL) in charge of porphyrin transport, which are highly expressed in cancer cells. However, most of photosensitizers are insoluble and exhibit side effects in human body due to phototoxicity demonstrated by a long retention time. In addition, the photosensitizer based therapy requiring irradiation of an appropriate amount of light (photon) has a disadvantage in that it cannot be used for large-sized tumor cells due to a limitation in light delivery.

Therefore, in order to enhance therapeutic effects, two therapies of photodynamic therapy (PDT) and drug therapy using gene, anti-cancer medicine or protein drug may be combined, instead of singly performing the photodynamic therapy (PDT) or the drug therapy.

In the conventional therapy, the gene, anti-cancer medicine or protein drug gene is not delivered to a target portion at the same time with the photosensitizer but is subjected to photon irradiation a predetermined time after the photosensitizer is injected. In the conventional therapy, various kinds of drugs should be injected many times, and it is impossible to transfer the drugs specifically to the lesion portions. In addition, since the photosensitizer and the therapeutic drug are not formed in a single body, they may not be positioned on the same part in a cell.

SUMMARY OF THE INVENTION

An aspect of the present invention relates to a gene nanocomposite including a photosensitizer-conjugated polymer; and one or more materials selected from a gene and a gene/cationic polymer composite.

Another aspect of the present invention relates to a method for producing a gene nanocomposite, the method including preparing a photosensitizer-conjugated polymer by conjugating a photosensitizer with a polymer; and mixing the photosensitizer-conjugated polymer and one or more of a gene and a gene/cationic polymer composite.

Still another aspect of the present invention relates to a cellular internalization method of a gene, including processing a cell with the gene nanocomposite of one of claims 1 to 15; and irradiating light to the cell.

The advantageous effects of the present invention are not limited to those described herein and will become apparent by reference to the following detailed description of exemplary embodiment of the present invention.

BRIEF DESCRIPTION OF DRAWINGS

For a better understanding of the present disclosure, preferred embodiments thereof are now described, purely by way of non-limiting example and with reference to the attached drawings, wherein.

DETAILED DESCRIPTION OF ILLUSTRATIVE EMBODIMENTS

Figure 1:
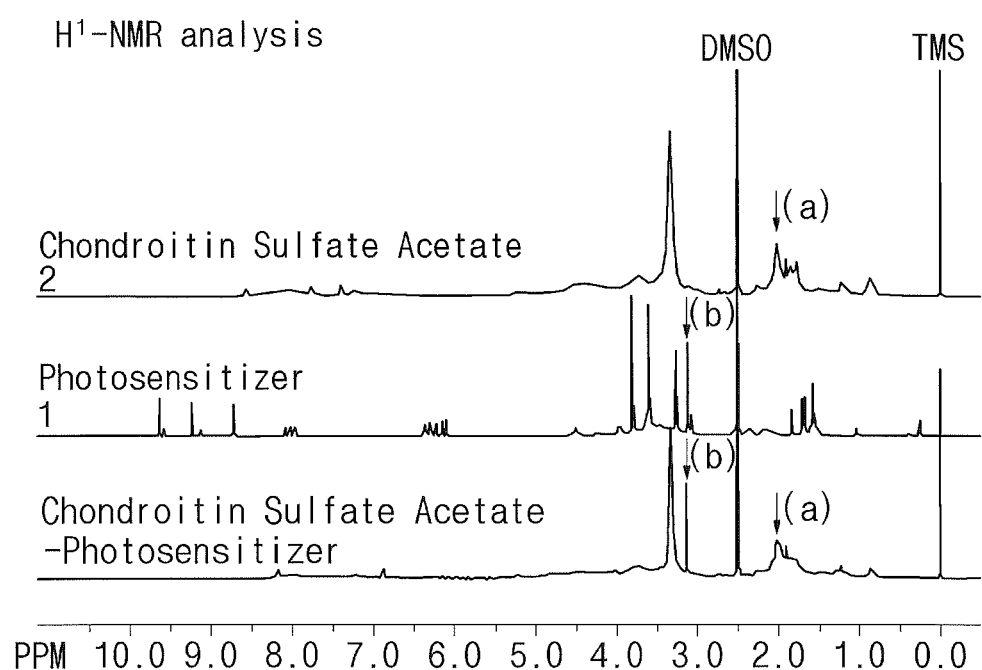
FIG. 1 illustrates a H1-NMR analysis of polyethyleneimine-photosensitizer conjugates (A) and acetylated chondroitin sulfate-photosensitizer conjugates (B) according to Examples 1 to 3 of the present invention.

Hereinafter, embodiments of the present invention will be described in more detail with reference to the accompanying drawings.

The present invention provides a gene nanocomposite including a photosensitizer-conjugated polymer. More particularly, the present invention provides a gene nanocomposite including a photosensitizer-conjugated polymer; and one or more of a gene and a gene/cationic polymer composite.

Gene Nanocomposite

The nanocomposite can be used for cellular internalization of a gene. More specifically, when the nanocomposite having a photosensitizer, a gene and a polymer incorporated into a single body is processed on a cell, it is absorbed into the cell through receptor-mediated endocytosis. In addition, in order to avoid decomposition of the gene by various enzymes present in endosome or lysosome, the photosensitizer may be excited by irradiating photon and generation of activated oxygen may be caused due to excitation of the photosensitizer, resulting in disruption of endosome or lysosome. Accordingly, decomposition of the genetic by the nanocomposite in cells can be avoided and cellular internalization efficiency of the gene can be improved. In addition to the gene, various physiologically active materials may further be added to be employed to gene therapy.

The gene nanocomposite is produced by electrostatic interaction between the photosensitizer-conjugated polymer and the gene and/or the gene/cationic polymer composite. For example, the gene nanocomposite may be an ionic composite. More specifically, the gene nanocomposite having the gene, the photosensitizer and the polymer incorporated into a single body may be produced by electrostatic interaction between the photosensitizer-conjugated polymer demonstrating an anionic property and the gene and/or the gene/cationic polymer composite demonstrating a cationic property.

In addition, the nanocomposite having the gene, the photosensitizer and the polymer incorporated into a single body may be produced by electrostatic interaction between the photosensitizer-conjugated polymer demonstrating a cationic property and the gene and/or the gene/cationic polymer composite demonstrating an anionic property.

The gene nanocomposite may have a particle size of 400 nm or less, preferably 300 nm or less, and more preferably in a range of 50 nm to 300 nm.

Photosensitizer-Conjugated Polymer

The photosensitizer-conjugated polymer may form a gene nanocomposite having the gene and/or the gene/polymer composite, the photosensitizer and the polymer incorporated into a single body and may more safely cause cellular internalization of the gene.

The photosensitizer-conjugated polymer is formed by conjugating the photosensitizer with one or more selected from the group consisting of cationic and anionic polymers, preferably an anionic polymer. The polymer has a weight average molecular weight of 100 to 100,000. In the photosensitizer-conjugated polymer, the anionic polymer may be one or more selected from the group consisting of chondroitin-6-sulfate (C6S), heparan sulfate (HS), heparan sulfate proteoglycan (HSPG), heparin, chondroitin-4-sulfate (C4S), chondroitin-6-sulfate (C6S), dermatan sulfate (DS), keratan sulfate (KS) and hyaluronic acid (HA). Preferably, the anionic polymer is chondroitin-6-sulfate (C6S) having a repeating unit of 20 to 100.

The cationic polymer may be one or more selected from the group consisting of linear or branched polyethyleneimine (PEI), glycol chitosan (GC), chitosan, poly-L-lysine (PLL), poly-beta-amino ester polymer, polyamidoamine (PAMAM) dendrimer and derivatives thereof, preferably polyethyleneimine.

The photosensitizer is excited by absorbing light having a particular wavelength and reacts with a substrate or oxygen around the same in an excited state to generate activated oxygen. Any photosensitizer can be used without limitation so long as it can be employed to human body. Specifically, the photosensitizer may be one or more selected from the group consisting of porphyrins, chlorines, bacteriochlorines, phthalocyanines, naphthalocyanines and 5-aminolevuline esters, preferably a porphyrin-series compound. More specifically, the photosensitizer may be benzoporphyrin, meso-tetraphenylporphyrin, meso-tetra (4-sulfonatophenyl) porphine), pheophytin a, pheophorbide a, chlorin e6, tetrasulfophthalocyanine, aluminum phthalocyanine, and so on.

Gene and Gene/Polymer Composite

Any gene can be used without limitation so long as it can be employed to gene therapy, preferably, a gene encoding green fluorescence protein (GFP) and a therapeutic gene demonstrating anti-cancer effects, such as Si-RNA or Sh-RNA. In addition, the gene may include physiologically active materials that can be employed to various gene therapies. More specifically, the therapeutic gene may include epidermal growth factor receptor (EGFR) sh-RNA suppressing an EGFR gene, and the physiologically active materials may include oligoouncleotide, ribozyme, plasmid, and antisense DNA. The gene of the present invention may include one or more of the aforementioned genes physiologically active materials/

The gene/cationic polymer composite is formed by electrostatic interaction between a negatively charged gene and a cationic polymer. The gene is the same as described above. The cationic polymer has a weight average molecular weight of 100 to 100,000, and examples thereof may include one or more selected from the group consisting of linear or branched polyethyleneimine (PEI), glycol chitosan (GC), chitosan, poly-L-lysine (PLL), poly-beta-amino ester polymer, polyamidoamine (PAMAM) dendrimer and derivatives thereof, preferably polyethyleneimine.

The gene/cationic polymer composite may have a particle size of 300 nm or less, preferably 200 nm or less, and more preferably in a range of 50 nm to 250 nm.

The present invention provides a method of producing the gene nanocomposite.

The method of producing the gene nanocomposite includes preparing a photosensitizer-conjugated polymer and mixing the same.

In the preparing of the photosensitizer-conjugated polymer, the photosensitizer is conjugated with the polymer. The photosensitizer and the polymer are the same as described above. In the preparing of the photosensitizer-conjugated polymer, ratio of the photosensitizer to the polymer is in a range of 1:1 to 1:30 (mol/mol), preferably 1:1 to 1:10, and more preferably 1:1 to 1:5 (mol/mol). When the mixing ratio is within the range stated above, it is possible to avoid a change in the polymer characteristics due to the presence of the photosensitizer, which may impede formation of gene nanocomposite, such as a change in the structure and charge of the polymer, while suppressing toxicity from being caused to cells due to the photosensitizer or the polymer.

In the mixing, one or more of the gene and the gene/cationic polymer composite and the photosensitizer-conjugated polymer are mixed for reaction to take place, thereby preparing the composite.

In the mixing, a mixing ratio of the photosensitizer-conjugated polymer to the one or more of the gene and the gene/cationic polymer composite is in a range of 1:0.1 to 1:100 (w/w), preferably 1:0.5 to 1:70 (w/w). When the mixing ratio is within the range stated above, it is possible to facilitate formation of gene nanocomposite by electrostatic interaction between the photosensitizer-conjugated polymer and the gene and/or the gene/cationic polymer composite and generation of activated oxygen in the presence of the photosensitizer, thereby improving cellular internalization efficiency and gene expression efficiency.

In the mixing, the photosensitizer-conjugated polymer; and one or more of the gene and the gene/cationic polymer composite are mixed to allow a reaction to take place at a temperature of 18 to 37° C. for 20 minutes to one hour.

In addition, in the mixing of the gene/cationic polymer composite, there may further be provided preparing the gene/cationic polymer composite after the preparing of the photosensitizer-conjugated polymer. In the preparing of the gene/cationic polymer composite, the gene/cationic polymer composite is prepared by electrostatic interaction between the gene and the cationic polymer by mixing the gene and the cationic polymer. For example, the gene/cationic polymer composite may be, for example, an ion composite of the gene and the cationic polymer. In the preparing of the polymer composite, the N/P ratio (Number of nitrogen atoms in the cationic polymer/Number of phosphate salt atoms in the gene) is in a range of 0.1 to 100, preferably 0.1 to 50. When the N/P ratio is within the range stated above, it is possible to facilitate gene stabilization by the cationic polymer, thereby increasing cell absorption efficiency and forming a stable gene nanocomposite.

The present invention provides a cellular internalization method of a gene using the gene nanocomposite.

The cellular internalization method can improve gene expression efficiency by inducing cellular internalization of a gene by combining gene therapy and photodynamic therapy (PDT), thereby maximizing the gene therapy effect.

The cellular internalization method includes processing a cell with a gene nanocomposite, and irradiating light to the cell.

The processing of the gene may include incubating at room temperature to 50° C., preferably at room temperature to 40° C., for 10 minutes to 24 hours, preferably 10 minutes to 10 hours. The room temperature is not particularly limited but is in a range of 15 to 25° C.

In the processing of the gene nanocomposite, the content of the gene nanocomposite may be appropriately selected according to the kind of cell, patient's condition, therapy and so on. The content of the gene nanocomposite is preferably in a range of 0.01 mg to 10 mg/kg body weight.

In the processing of the gene nanocomposite, the cell may be a mammal-derived cell, and specific examples of the mammal-derived cell may include at least one selected from the group consisting of cancer cells of squamous cell carcinoma, uterine cancer, cervical cancer, prostate cancer, head and neck cancer, pancreatic cancer, brain cancer, breast cancer, liver cancer, skin cancer, esophageal cancer, testicular cancer, kidney cancer, colorectal cancer, rectal cancer, stomach cancer, bladder cancer, ovarian cancer, and gallbladder cancer; mesenchymal stem cell, hematopoietic stem cell, nervous stem cell and adipose stem cell.

The irradiating of the light source includes exciting the photosensitizer by irradiating the light source into the cell processed with the gene nanocomposite, generating activated oxygen by exciting the photosensitizer, thereby causing disruption of endosome or lysosome secreting an enzyme for decomposing the gene in the cell and enhancing cellular internalization of the gene.

In the irradiating of the light source, the wavelength, intensity and irradiation amount of photon may be appropriately adjusted according to the kind and processed amount of the photosensitizer and the kind of cell. The light source having a wavelength of 500 to 700 nm may be irradiated with energy of 200 $J/cm^2$ or less, specifically 0.1 to 200 $J/cm^2$, preferably 0.1 to 20 $J/cm^2$, more preferably 0.1 to 10 $J/cm^2$, and most preferably 0.1 to 2 $J/cm^2$, thereby lowering toxicity of cells while inducing sufficiently high activity of the photosensitizer.

The cellular internalization method can be used for gene therapy. More particularly, the cellular internalization method can be used for gene therapies for curing hereditary diseases cardiovascular diseases, immune diseases, endocrine diseases, or cancers, or a therapy using stem cells.

Hereinafter, the present invention will be described in more detail through the following Examples and Comparative Examples. However, the following examples are provided merely for purposes of illustration of certain aspects and embodiments of the present invention, and are not intended to limit the invention.

Example 1

Conjugation of Polyethyleneimine Photosensitizer 50 mg of a photosensitizer having the chemical formula (1) was dissolved in dimethyl sulfoxide (DMSO) with N-hydroxysuccinimide (HoSu) and N,N'-Dicyclohexylcarbodiimide (DCC). Dicyclohexylurea (DCU) resulting after the reaction for 6 hours was removed using a filter, and other reaction products were mixed with 100 mg of polyethyleneimine (MW25000) dissolved in DMSO, following by reacting for 24 hours. The reactant liquid was dialyzed with primary distilled water for two days using a dialysis membrane (Spectra/Por; mol. wt. cutoff size, 1000). After dialysis, the reactant product was freeze-dried, thereby acquiring a polyethyleneimine-photosensitizer conjugate having the chemical formula (2):

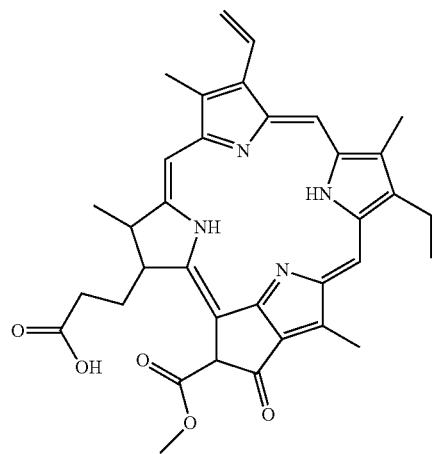

(1)

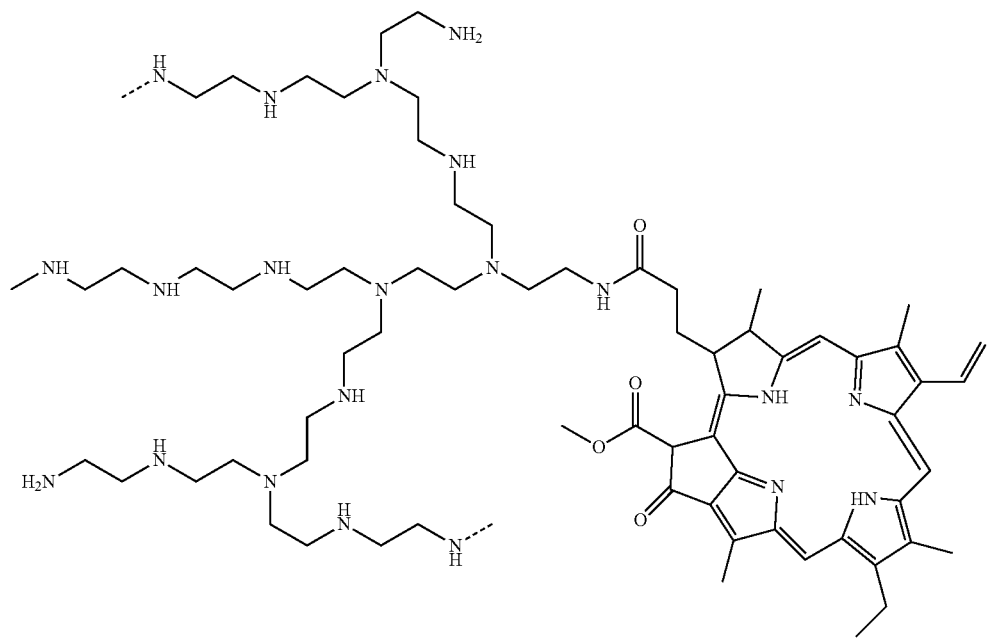

(2)

Example 2

Acetylation of Anionic Polymer Chondroitin Sulfate 1 g of chondroitin sulfate (Carl ROTH, 5197, Germany) was dissolved in 10 ml of formamide (Kanto chemical, Japan) and 2 ml of pyridine (Junsei, Japan) was added, followed by adding 2 ml of acetic anhydride (Junsei, Japan) after 30 minutes. After reacting for 24 hours, the reactant liquid was dialyzed with primary distilled water for two days using a dialysis membrane (Spectra/Por; mol·wt. cutoff size, 3000). After dialysis, the reactant product was freeze-dried, thereby acquiring acetylated chondroitin sulfate having the chemical formula (3):

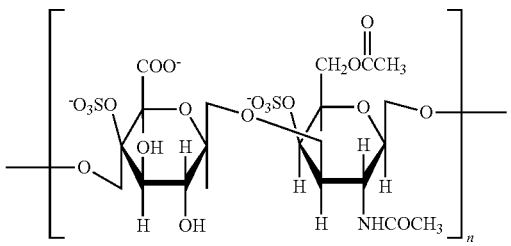

(3)

Example 3

Conjugation of Anionic Polymer Chondroitin Sulfate and Photosensitizer 0.1 g of acetylated chondroitin sulfate prepared in Example 2 was dissolved in 20 ml of DMSO. 5 mg of the photosensitizer having the chemical formula (1) was dissolved in DMSO and N,N'-Dicyclohexylcarbodiimide (DCC) and 4-dimethylaminopyridine (DMAP) were added to 1.5 times each in a molar ratio of the photosensitizer (?). The two obtained solutions were stirred at room temperature for 3 hours, following by reacting for 24 hours. In order to remove the unreacted photosensitizer, the resultant product was dialyzed with primary distilled water for two days using a dialysis membrane (Spectra/Por; mol·wt. cutoff size, 3000). After dialysis, the reactant product was freeze-dried, thereby acquiring a photosensitizer-conjugated anionic polymer having the chemical formula (4):

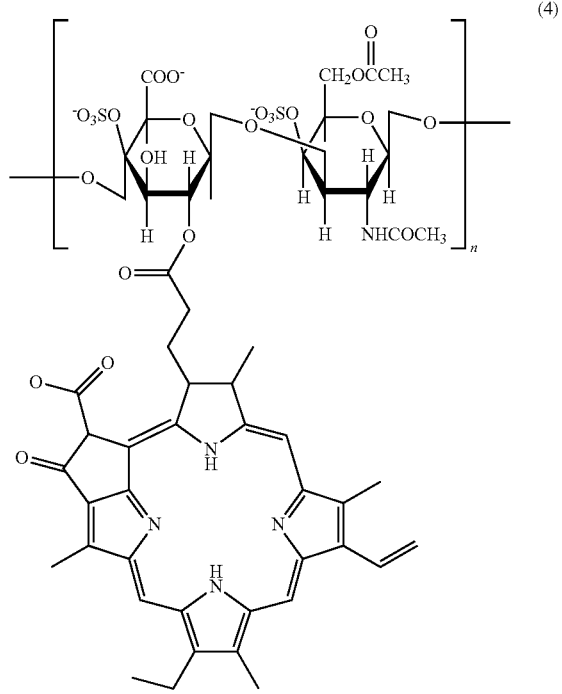

(4)

Example 4

Preparation of Ion Composite of Gene/Polyethyleneimine-Photosensitizer

In order to prepare an ion composite of gene/polyethyleneimine-photosensitizer, 2 μg of shRNA causing interference of green fluorescence protein (GFP) gene or an epidermal growth factor receptor (EGFR) gene, that is, EGFRshRNA, and 2 μg of polyethyleneimine-photosensitizer prepared in Example 1 were mixed with α-MEM (Minimum essential medium eagle alpha modification, hyclone, USA) without FBS (fetal bovine serum) included therein, following by reacting at room temperature for 10 minutes, thereby preparing the ion composite.

Example 5

Preparation of Ion Composite of Gene/Cationic Polymer and Anionic Polymer Photosensitizer First, a gene/cationic polymer composite was prepared in the following manner. In preparing the composite, a GFP gene or plasmid (Clontech, USA) was used, 2 μg of plasmid and 2 μg of polyethyleneimine were mixed with α-MEM (Minimum essential medium eagle alpha modification, hyclone, USA) without FBS included therein, following by reacting at room temperature for 10 minutes, thereby preparing the ion composite. In order to prepare an ion composite of gene/cationic polymer and anionic polymer photosensitizer, the gene/cationic polymer composite and the anionic polymer photosensitizer having the chemical formula (4) dissolved in α-MEM (alpha-minimum essential medium) without FBS included therein were mixed in mass ratios of 1:1, 1:5, 1:10 and 1:50, followed by incubating at room temperature for 30 minutes, thereby forming a nanocomposite.

Experimental Example 1

Verification of Conjugation of Photosensitizer of Acetylated-Chondroitin Sulfate In order to verify conjugation of acetated-photosensitizer of chondroitin sulfate, the conjugation of acetated-photosensitizer of chondroitin sulfate was confirmed by 1H-NMR (Avancek 300, Bruker, Germany) and the result thereof is shown in FIG. 1.

As shown in FIG. 1, a signal around 1.8-2.2 ppm was detected at 1H-NMR peak of chondroitin sulfate acetate, suggesting that chondroitin sulfate was successfully acetylated. In addition, a signal around 3.1-3.3 ppm, which is peculiar to the photosensitizer, was detected at 1H-NMR peak of chondroitin sulfate acetate-photosensitizer, suggesting that the photosensitizer was conjugated with the acetated chondroitin sulfate.

Experimental Example 2

Analysis of Particle Characteristics and Shapes of Nanocomposites

In order to analyze particle characteristics of nanocomposites depending on ratios of gene/polyethyleneimine-photosensitizer, gene/cation polymer composite and chondroitin sulfate acetate-photosensitizer, the nanocomposites were prepared in Examples 4 and 5 and particle characteristics thereof were analyzed using a Zetasizer Nano ZS system (Malvern Instruments Ltd, UK).

Figure 2:
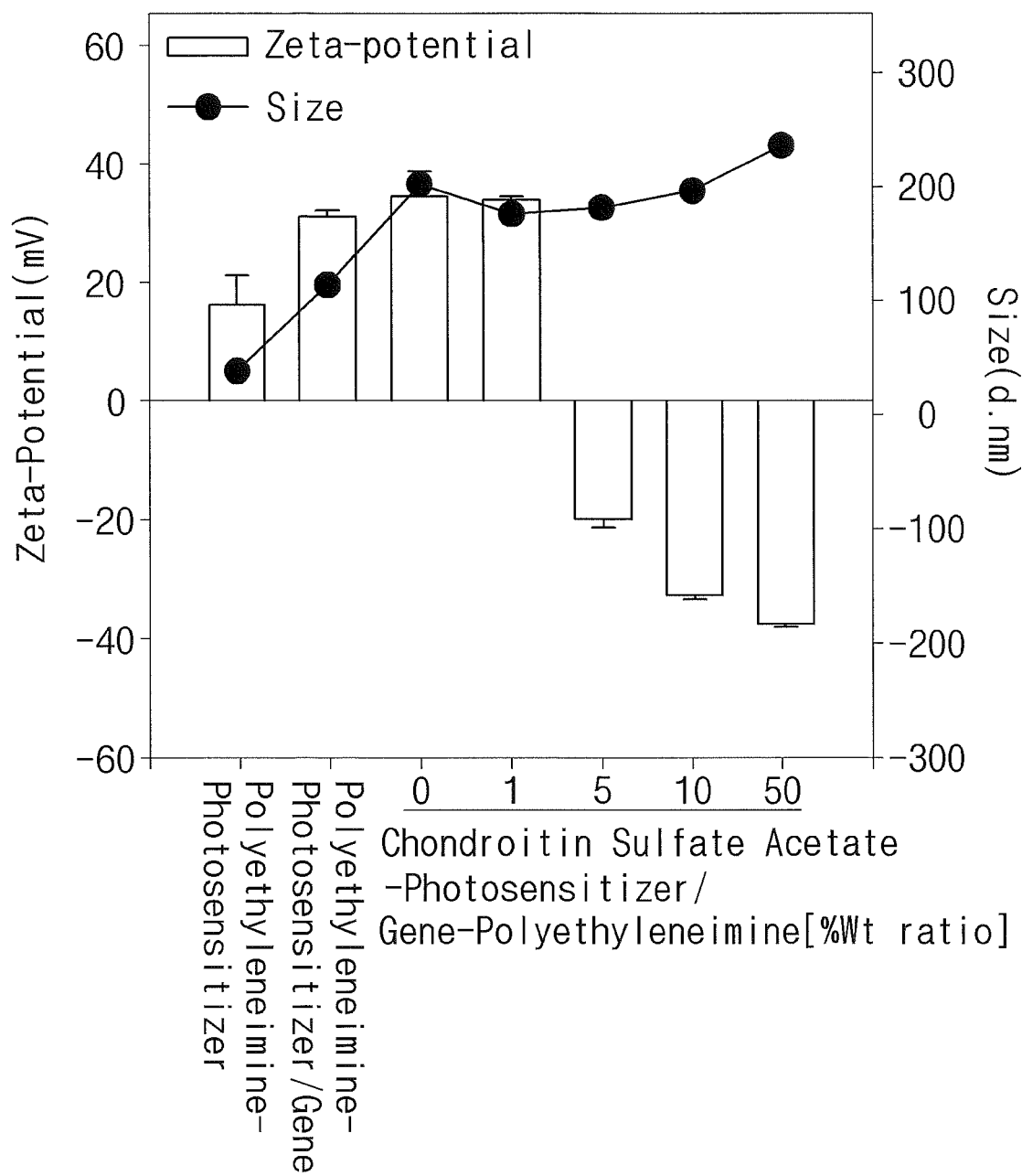
FIG. 2 illustrates particle characteristics of gene nanocomposites according to Examples 5 and 6 of the present invention.

As shown in FIG. 2, it was confirmed that the gene/polyethyleneimine-photosensitizer ion composite had a particle size of approximately 150 nm and a highly positive surface charge of +35 mV. In addition, it was confirmed that the ion composite of gene/cation polymer composite and chondroitin sulfate acetate-photosensitizer had a particle size of approximately 200 nm and a highly negative surface charge of approximately 18 to −40 according to the increase in the mass ratio of the anionic polymer photosensitizer. Based on the data of this experimental example, a mass ratio of the gene/cation polymer composite and anionic polymer photosensitizer used in Experimental Example 3 was fixed to 1:50.

Experimental Example 3

Transfection to Cancer Cell Using Nanocomposite and Photon Irradiation

In order to verify gene delivery efficiency of the ion composite of the gene/polyethyleneimine-photosensitizers prepared in Examples 4 and 5 and the ion composite of the gene/cation polymer composite and chondroitin sulfate acetate-photosensitizer (1:50 mass ratio), transfection of cancer cells was performed. The cells used were HCT-116 cells as human liver cancer cells, which are commercially available from Korean Cell Line Bank. The cells were suspended in RPMI-1640 (Roswell Park Memorial Institute 1640, hyclone, USA) including 10% FBS (fetal bovine serum) and 1% penicillin-streptomycin (Gibco, USA) and were transferred to culture dishes, followed by cultivating in 5% culture media maintained at 37° C. The human liver cancer cells (HCT-116) were transferred to 35 mm culture dishes for cultivation, and when the cultivated cells grew as much as 70% of the area of each culture dish, they were processed with the prepared nanocomposite. After 4 hours, near infrared laser (HeNe laser, 633 nm) with energy of 0 to 1.0 J/cm$^2$ was irradiated into the cells and then additionally cultivated for 24 hours in culture media maintained at 37° C., to confirm the gene expression efficiency.

Experimental Example 4

Verification of Green Fluorescence Protein (GFP) Expression of Mesenchymal Stem Cells by Western Blotting and Polymerase Chain Reaction (PCR)

In order to verify the efficiency of delivering green fluorescence protein (GFP) gene to HCT-116 cells using a photosensitizer and near infrared laser, expression of GFP was confirmed by western blotting and a PCR. For the western blotting, transfection to HCT-116 cells was performed in the same manner as in Experimental Example 3, and the cells were processed with trypsin-EDTA for collection of cells, followed by centrifuging at 1500 rpm for 5 minutes. After removing the supernatant solution, all proteins were isolated using a protein extraction buffer (40 Mm Tris-HCl, pH8.0, 120 mM NaCl, 0.5% NP-40, 2 µg/ml aprotinin, 2 µg/ml leupetin, 100 µg/ml PMSF). Amounts of all proteins were measured using a BCA protein assay kit (Thermo, USA).

The isolated proteins were weighed in the above-described manner, the same amount of a protein was loaded into a 12% SDS polyacrylamide gel for electrophoresis and then transferred with a PVDF membrane (Bio-Rad, USA) using a transblotting apparatus (Bio-Rad, USA). The PVDF membrane was incubated for 1.5 hours in 5% skimmed dry milk dispersed in TBS-T (25 mM Tris-HCL, pH7.4, 150 mM NaCl, 0.2% Tween 20), thereby preventing non-specific protein binding. Mouse anti-GFP was used as a primary antibody for incubating at 4° C. for 12 hours. Then, the resultant product was washed with TBS-T and incubated for 2 hours using anti-mouse goat IgG with horse radish peroxidase immunostaing (HRP) as a secondary antibody. The resultant product was washed again with TBS-T and protein bands were visualized using and enhanced chemiluminescence (ECL) solution and X-ray film.

In order to verify the expression efficiency of GFP mRNA through a PCR, the cells were processed with trypsin-EDTA for collection of cells, followed by centrifuging at 1500 rpm for 5 minutes. After removing the supernatant solution, 1 ml of a Trizol solution (Sigma, USA) was added to each sample, and the cells were softly smashed by pipetting, followed by adding 200 µl of chloroform and stirring. After incubating at room temperature for 5 minutes, the resultant product was subjected to centrifugation at 13000×g for 15 minutes at 4° C. Thereafter, the colorless supernatant solution was transferred to a new tube, and 500 µl of isopropyl alcohol was added thereto, followed by incubating for 10 minutes. The resultant product was subjected to centrifugation at 4° C. at 13000×g for 15 minutes to remove the supernatant solution and washed with 75% ethanol and pellets were dried for 5 minutes. The isolated RNA pellets were dissolved in distilled water processed with diethyl pyrocarbonate (DEPC)) and concentrations thereof were measured using a spectrophotometer.

Single stranded cDNA was synthesized from 1 µg of the extracted RNA using a single stranded cDNA synthesis kit (Intron, Korea). 1 µg of the extracted RNA having the composition as shown in Table 1 and sterile water were mixed such that a total quantity of the composition was adjusted to 9.5 µl and 1 µl of Oligo (dT) was then dropwise added. The resultant product was incubated at 75° C. for 5 minutes and was allowed stand undisturbed in ice for 1 minute. Thereafter, the reactant solution was mixed with the following composition and incubated two times under conditions of 42° C. and 60 minutes and 70° C. and 5 minutes, thereby synthesizing single stranded cDNA and diluting with sterile water.

TABLE 1

| Component | Content |
|---|---|
| RNase inhibitor | 1.0 µl |
| 5x RT buffer | 4.0 µl |
| dNTP | 2.0 µl |
| DTT | 2.0 µl |
| AMV RT enzyme | 0.5 µl |
| Total | 9.5 µl |

Experimental Example 5

Evaluation of EGFR shRNA Gene Delivery Efficiency

In order to evaluate the delivery efficiency of therapeutic genes, nanocomposites of EGFR shRNA, which inhibits EGFR gene expression effects, was prepared in the same manner as in Example 5 in a mass ratio of the gene/cationic polymer composite and the anionic polymer photosensitizer being 1:50, and transfection was performed on cells in the same manner as in Experimental Example 3. Thereafter, the EGFR gene suppressing effect was confirmed by a real time PCR.

In order to confirm the EGFR mRNA gene through the real time PCR, as described in Experimental Example 4, the cells were collected and a total amount of RNAs were extracted to synthesize cDNAs.

In order to perform the real time PCR, 2 µl of the synthesized cDNAs was taken to be mixed with EGFR gene primer and a SYBR green PCR master mix for real time PCR. Then, mRNA expression was observed by a real-time PCR System (Applied Biosystems, Warrington, UK). Gene primers for the real time PCR are the same as listed in Table 2.

2 µl of cDNA synthesized to perform a polymerase chain reaction (PCR) was taken to be mixed with a GFP DNA primer and a Taq polymerase, the resultant mixture was then allowed to stand undisturbed at 95° C. for 5 minutes to inhibit activity of other enzymes, and 32 cycles of PCRs were repeatedly performed under conditions of 95° C. and 1.5 minutes, 60° C. and 1 minute, and 72° C. and 2 minutes for chain polymerizing DNAs.

DNA sequences of the primers used in the reaction scheme are listed in Table 2, and β-actin primers were used as control groups. The PCR product was confirmed by electrophoresis using 1% agarose gel by taking 5 µl of the resultant product.

TABLE 2

| Gene | Primer for PCR | Base sequence |
|---|---|---|
| GFP | Sense | TGA ACC GCA TCG AGC TGA AGG G |
|  | Antisense | TCC AGC AGG ACC ATG TGA TCG C |
| EGFR | Sense | ATG CTC TAC AAC CCC ACC AC |
|  | Antisense | GCC CTT CGC ACT TCT TAC AC |
| β-actin | Sense | CCA CGA AAC TAC CTT CAA CTC C |
|  | Antisense | TCA TAC TCC TGC TGC TTG CTG ATC C |

Figure 3:
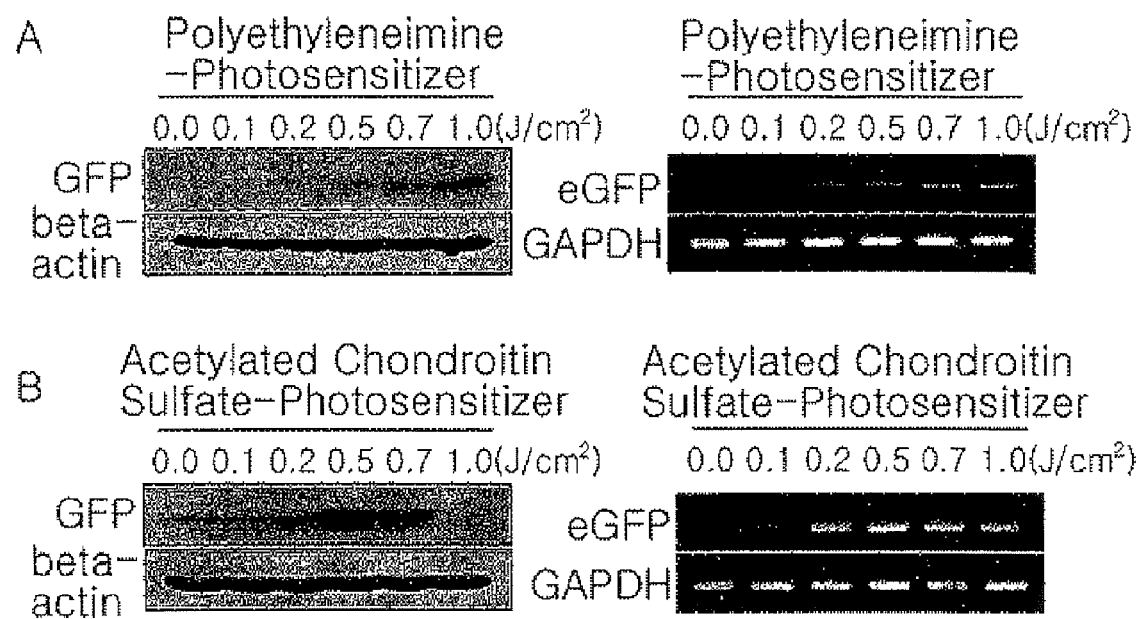
FIG. 3 illustrates expression of green fluorescence protein (GFP) and green fluorescence protein mRNA in HCT-116 cells according to Experimental Example 4 of the present invention, as confirmed by western blotting (A) and a polymerase chain reaction (PCR) (B)

As shown in FIG. 3 (A) showing results of western blotting and PCR, in the gene/polyethyleneimine-photosensitizer ion composite, expression of green fluorescence protein (GFP) was increased with laser irradiation, exhibiting a relatively thick band.

In addition, as shown in FIG. 3 (B), in the gene/cation polymer composite and anionic polymer composite, expression rates of GFP were increased with laser irradiation, compared to a control group without laser irradiation. When laser was irradiated with energy of 0.5 J/cm$^2$, the expression rate was highest. In addition, it was confirmed that the gene expression rate was higher in test groups of gene/cation polymer composite and chondroitin sulfate acetate-photosensitizer ion composites than in groups of the gene/polyethyleneimine-photosensitizer ion composite processed and irradiated with laser. Therefore, in the following experiments, gene delivery was performed using gene/cation polymer composite and chondroitin sulfate acetate-photosensitizer ion composites.

Figure 4:
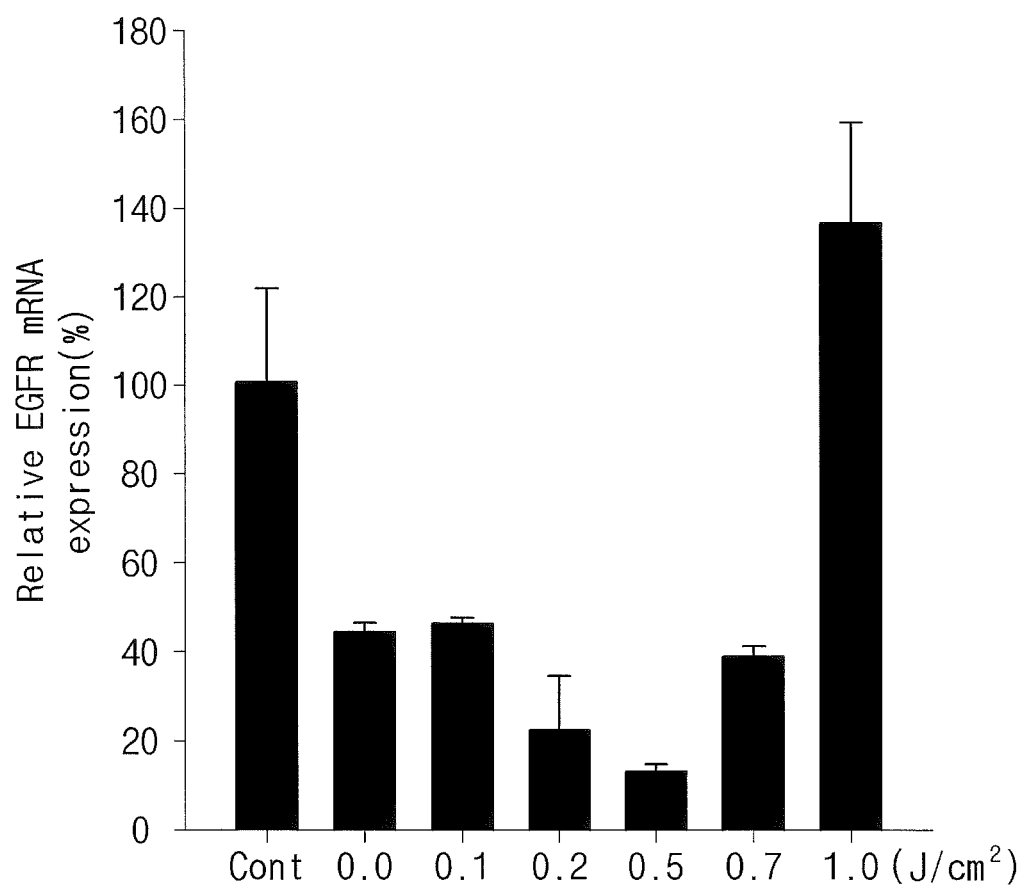
FIG. 4 illustrates suppression effects of expression of EGFR protein and mRNA in HCT-116 cells according to Experimental Example 5 of the present invention, as confirmed in real time by western blotting (A) and a polymerase chain reaction (PCR) (B).

As shown in FIG. 4 showing results the real-time PCR result, EGFR mRNA expression was suppressed most with irradiation of laser with energy of 0.5 J/cm$^2$, compared to the control group without laser irradiation. Here, approximately 20% or less of EGFR mRNA expression was suppressed.

Technical Problems

Exemplary embodiments of the present invention have been made in an effort to solve the problems of the prior art, and provide a gene nanocomposite and a cellular internalization method of a gene using the same, which can improve cellular internalization efficiency of a gene into a mammal-derived cell by incorporating a photosensitizer and a gene used in photodynamic therapy (PDT) and can improve gene expression efficiency.

Advantageous Effects

As described above, according to exemplary embodiments of the present invention, a gene nanocomposite is formed by incorporating a photosensitizer, a gene and an ionic polymer by employing a photosensitizer-conjugated polymer used in photodynamic therapy (PDT), cellular internalization efficiency of the gene can be improved by using the gene nanocomposite, and gene expression efficiency can be improved. In addition, a physiologically active material is further added to the nanocomposite, so that exemplary embodiments of the present invention can be applied to gene therapy based on transfer of various genes in treating various diseases. It is understood that the examples and embodiments described herein are for illustrative purposes only and that various modifications or changes in light thereof will be suggested to persons skilled in the art and are to be included within the spirit and purview of this application and scope of the appended claims.

The invention claimed is:

1. A gene nanocomposite comprising:
   a photosensitizer-conjugated polymer wherein the photosensitizer is excited by an irradiating photon resulting in generation of activated oxygen and is pheophorbide a; and
   one or more materials selected from therapeutic gene, a therapeutic gene/cationic polymer composite, or a combination thereof, wherein the therapeutic gene is si-RNA or sh-RNA.

2. The gene nanocomposite of claim 1, wherein the photosensitizer-conjugated polymer is prepared by conjugating the photosensitizer with one or more selected from the group consisting of cationic and anionic polymers.

3. The gene nanocomposite of claim 2, wherein in the photosensitizer-conjugated polymer, the anionic polymer is one or more selected from the group consisting of chondroitin-6-sulfate (C6S), heparan sulfate (HS), heparan sulfate proteoglycan (HSPG), heparin, chondroitin-4-sulfate (C4S), chondroitin-6-sulfate (C6S), dermatan sulfate (DS), keratan sulfate (KS) and hyaluronic acid (HA).

4. The gene nanocomposite of claim 2, wherein in the photosensitizer-conjugated polymer, the cationic polymer is one or more selected from the group consisting of linear or branched polyethyleneimine (PEI), glycol chitosan (GC), chitosan, poly-L-lysine (PLL), poly-beta-amino ester polymer, polyamidoamine (PAMAM) dendrimer and derivatives thereof.

5. The gene nanocomposite of claim 1, wherein in the therapeutic gene/cationic polymer composite, the cationic polymer has a weight average molecular weight of 100 to 100,000.

6. The gene nanocomposite of claim 1, wherein in the therapeutic gene/cationic polymer composite, the cationic polymer is one or more selected from the group consisting of linear or branched polyethyleneimine (PEI), glycolchitosan (GC), chitosan, poly-L-lysine (PLL), poly-beta-amino ester polymer, polyamidoamine (PAMAM) dendrimer and derivatives thereof.

7. The gene nanocomposite of claim 1, wherein in the therapeutic gene/cationic polymer composite, an N/P ratio, which is a number of nitrogen atoms in the cationic polymer to a number of phosphate salt atoms in the gene, is in a range of 0.1 to 100.

8. The gene nanocomposite of claim 1, wherein in the gene nanocomposite, a mixing ratio of a therapeutic gene and a photosensitizer-conjugated polymer in the therapeutic gene/cationic polymer composite is 1:0.1 to 1:100 (w/w).

9. The gene nanocomposite of claim 1, wherein the gene nanocomposite has a particle size of 400 nm or less.

10. The gene nanocomposite of claim 1, wherein the gene nanocomposite comprises a photosensitizer-conjugated cationic polymer; and the therapeutic gene.

11. The gene nanocomposite of claim 1, wherein the gene nanocomposite comprises: a photosensitizer-conjugated anionic polymer; and the therapeutic gene/cationic polymer composite.

12. The gene nanocomposite of claim 1, wherein the gene nanocomposite is used for cellular internalization of the therapeutic gene.

* * * * *

UNITED STATES PATENT AND TRADEMARK OFFICE
CERTIFICATE OF CORRECTION

PATENT NO.        : 9,765,335 B2
APPLICATION NO.   : 14/364611
DATED             : September 19, 2017
INVENTOR(S)       : Kun Na and Sin Jung Park It is certified that error appears in the above-identified patent and that said Letters Patent is hereby corrected as shown below:

On the Title Page

In Assignee item (73), please replace "CATHOLIC UNIVERSITY OF KOREA INDUSTRY-ACADEMIC COOPERATION FOUNDATION" with --CATHOLIC UNIVERSITY OF KOREA INDUSTRY-ACADEMY COOPERATION FOUNDATION--.

Signed and Sealed this
Fourteenth Day of May, 2019

Andrei Iancu
*Director of the United States Patent and Trademark Office*